(12) United States Patent
Prater et al.

(10) Patent No.: US 8,680,467 B2
(45) Date of Patent: *Mar. 25, 2014

(54) HIGH FREQUENCY DEFLECTION MEASUREMENT OF IR ABSORPTION WITH A MODULATED IR SOURCE

(75) Inventors: Craig Prater, Santa Barbara, CA (US); Kevin Kjoller, Santa Barbara, CA (US)

(73) Assignee: Anasys Instruments Corp., Santa Barbara, CA (US)

( * ) Notice: Subject to any disclaimer, the term of this patent is extended or adjusted under 35 U.S.C. 154(b) by 281 days.

This patent is subject to a terminal disclaimer.

(21) Appl. No.: 13/236,115

(22) Filed: Sep. 19, 2011

(65) Prior Publication Data

US 2013/0036521 A1 Feb. 7, 2013

Related U.S. Application Data

(63) Continuation-in-part of application No. 13/135,956, filed on Jul. 18, 2011, which is a continuation of application No. 11/803,421, filed on May 15, 2007, now Pat. No. 8,001,830.

(51) Int. Cl.
*G01J 5/00* (2006.01)
*G01Q 70/08* (2010.01)
*G01L 9/00* (2006.01)

(52) U.S. Cl.
USPC .............................. 250/338.1; 850/56; 73/705

(58) Field of Classification Search
USPC .............................. 250/338.1; 850/56; 73/705
See application file for complete search history.

(56) References Cited

U.S. PATENT DOCUMENTS

| 6,381,480 | B1 * | 4/2002 | Stoddart et al. ............... 600/338 |
| 6,823,724 | B1 * | 11/2004 | Kobayashi et al. ............. 73/105 |
| 6,985,818 | B1 * | 1/2006 | Samuels .......................... 702/22 |
| 2004/0020279 | A1 * | 2/2004 | Degertekin et al. ............. 73/105 |
| 2004/0099815 | A1 * | 5/2004 | Sfez et al. .................. 250/492.1 |

FOREIGN PATENT DOCUMENTS

WO WO2007030737 * 3/2007

* cited by examiner

*Primary Examiner* — David Porta
*Assistant Examiner* — Abra Fein
(74) *Attorney, Agent, or Firm* — Mark Rodgers (57) ABSTRACT

A method of obtaining submicron resolution IR absorption data from a sample surface. A probe microscope probe interacts with the sample surface while a tunable source of IR radiation illuminates the sample-tip interaction region. The source is modulated at a frequency substantially overlapping the resonant frequency of the probe and may be modulated at the contact resonance frequency of the probe when the probe is in contact with the sample surface. The modulation frequency is continually adjusted to account for shifts in the probe resonant frequency due to sample or other variations. A variety of techniques are used to observe such shifts and accomplish the adjustments in a rapid manner.

14 Claims, 9 Drawing Sheets

Fig. 9

HIGH FREQUENCY DEFLECTION MEASUREMENT OF IR ABSORPTION WITH A MODULATED IR SOURCE

CROSS REFERENCE TO RELATED APPLICATION

This application is a Continuation-in-Part of U.S. application Ser. No. 13/135,956 filed Jul. 18, 2011 which is a Continuation of U.S. application Ser. No. 11/803,421 filed May 15, 2007 now U.S. Pat. No. 8,001,830

STATEMENT REGARDING FEDERALLY SPONSORED RESEARCH OR DEVELOPMENT

Not Applicable

BACKGROUND OF THE INVENTION

In the parent applications of the current application measurements are described of absorption spectra from sub-micron regions of a sample surface, using a tunable infrared source to illuminate a region of the sample while recording the absorption of IR radiation with a cantilever probe of a probe microscope. The various techniques associated with these measurements are known as AFM-IR. One technique previously disclosed is to modulate or pulse the tunable infrared source at a frequency corresponding to a resonance of the microscope probe, typically a cantilever. In one embodiment, the infrared source is pulsed at a contact resonant frequency of the cantilever. Useful results have been demonstrated employing this technique by Mikhail Belkin and colleagues; F. Lu and M. A. Belkin, "Infrared absorption nano-spectroscopy using sample photoexpansion induced by tunable quantum cascade lasers," Opt. Express, in press (2011).

The Inventors have observed however that for some probe microscope configurations and/or samples of interest, the resonant frequency, especially the contact resonant frequency can vary over time and/or over different regions of the sample. The contact resonant frequency can change, for example, due to elastic and dissipative variations in the sample, topographic variations that give rise to different tip-surface contact area, changes in tip-surface interaction force, changes in lateral or longitudinal stresses on the cantilever, and other issues.

It is the object of the current invention to extend the techniques of modulating the IR source at or near a probe resonant frequency, including contact resonant frequencies, to the cases where the resonant frequency shifts significantly over time or relative positioning on the sample.

SUMMARY OF THE INVENTION

The invention is a method of obtaining measurements of infrared absorption of sub-micron regions of a sample with a probe microscope employing a cantilever probe with a tip, including the steps of illuminating a region of a sample with a tunable source of infrared radiation, interacting the probe tip with a surface of the sample, adjusting repeatedly a modulation frequency of the source of infrared radiation such that the modulation frequency substantially overlaps a resonant frequency of the cantilever probe and remains substantially overlapped as the cantilever resonant frequency shifts, and measuring a probe response resulting from absorption of infrared radiation by the sample.

In some embodiments, the resonant frequency corresponds to a contact resonance of the cantilever probe in contact with the sample surface. In some embodiments, the tunable source of infrared radiation is at least one of a quantum cascade laser and an optical parametric oscillator.

In other embodiments, the method is repeated at a plurality of wavelengths of the tunable source of infrared radiation to create an absorption spectrum of the submicron region of the sample and may be repeated at a plurality of positions on the sample surface to create an absorption map of the sample surface.

In certain embodiments, the contact resonant frequency of the cantilever probe is selected by performing a thermal tune of the cantilever probe. In some versions, the thermal tune is performed in less than 1 second or possibly less than 0.1 second.

In certain embodiments, the thermal tune is performed by recording data indicative of a deflection of the cantilever over a period of time, performing a fast Fourier transform on the data and repeating. Then the fast Fourier transforms are averaged using root mean square averaging and a resonant frequency of the cantilever probe from a peak in the averaged fast Fourier transform is identified.

In another embodiment the invention is a method of obtaining measurements of infrared absorption of sub-micron regions of a sample with a probe microscope employing a cantilever probe with a tip including the steps of illuminating a region of a sample with a quantum cascade laser, interacting the probe tip with a surface of the sample, measuring a thermal tune of the cantilever probe to determine a contact resonant frequency of the cantilever probe, adjusting a pulse frequency of the quantum cascade laser such that the pulse frequency substantially overlaps a resonant frequency of the cantilever probe, and measuring a probe response resulting from absorption of infrared radiation by the sample. In some embodiments the invention includes the step of repeating the above so as to account for contact resonant frequency shifts of the cantilever probe. In some versions the contact frequency shifts are due to variations in least one of: sample elastic modulus, tip-sample contact area, normal tip-sample force, or lateral tip-sample force.

Various embodiments may include covering the surface of the sample in fluid so that the tip-sample interaction is within fluid.

DETAILED DESCRIPTION OF THE INVENTION

The AFM-IR technique is described in the parent applications of the current application. To review, pulses from an infrared light source are directed at a sample to illuminate a region of the sample. When the wavelength of the IR light corresponds to an absorption of the sample, a portion of the IR light is absorbed. The absorbed heat causes a thermal expansion pulse at the surface of the sample which in turn can excite resonant oscillation of an AFM probe, typically a cantilever, that is interacting with the sample. Measuring the amplitude of the induced oscillation is indicative of the amount of IR absorption by the sample. By performing measurements at a plurality of wavelengths it is possible to create absorption spectra from sub-micron regions of a sample. Measuring the absorption at one or more wavelengths at a plurality of points on a surface can provide spatially resolved absorption measurements. Such measurements can be used to create profiles, maps, and images of IR absorption and can provide information about distribution of chemical species on the micro and nano scale.

Several sources have been used for AFM-IR. These include free electron lasers, optical parametric oscillators, and quantum cascade lasers (QCLs), for example. In certain of previous AFM-IR disclosure the IR source is pulsed at a repetition rate much lower than the resonant frequency, a few Hz using free electron lasers for example. In this mode of operation, the thermal expansion pulsed from the IR absorption induces a resonant pulse response. That is, the probe response includes a sharp onset of oscillation, often at several frequencies, and then an exponential decay, or "ringdown". The amplitude of the ringdowns are analyzed as a measure of the IR absorption. Note "probe" and "cantilever" are used interchangeably herein but it is to be understood that the invention applies to any probe microscope with a probe that is capable of resonant behavior in typical measurement scenarios.

QCLs and certain OPO's are a particularly interesting alternative source because of their compact size and high pulse repetition rates. Thus in the parent applications, the current applicant introduced the idea of generating IR pulses from a QCL (or OPO) at a rate corresponding to a resonant frequency of the AFM cantilever. This has the advantage of generating continuous oscillation of the cantilever. Thus smaller oscillation amplitudes may be detected versus the pulse-ringdown technique. As pointed out by Mikhail Belkin et al, such operation of the AFM-IR set-up may allow operation with lower pulse energy and hence smaller temperature rise in the sample.

However for some set-ups and/or samples the resonant frequencies of the cantilever may vary as a function of the position and the set-up conditions. For example, in the case of contact resonance frequencies (where the AFM is operated in contact mode), the resonant frequencies can be a function of the sample elasticity as well as the contact area, interaction force, adhesion, surface topography, and lateral forces in the tip-sample contact. The contact resonant frequencies can thus shift as a function of time and tip-sample position. These shifts may be especially problematic on heterogeneous samples with regions of significant variation in elastic modulus, where the contact resonant frequency can change by many kHz over small distances (e.g. a few 10 s of nanometers or a few micrometers) across a sample surface. Even on homogeneous samples or measurements at a single location, variations in tip-sample force from thermal effects can cause changes in contact resonant. With conventional AFM feedback, these effects can result in shifts of several kHz over the course of less than a minute in some measurement environments.

To be able to obtain robust absorption spectra and absorption maps it is desirable to maintain the modulation frequency at a frequency corresponding to a resonance of the cantilever throughout any variation in the sample or variation in set-up conditions.

The current invention involves techniques for dynamically adjusting the pulse frequency of a QCL or similar IR source such that the pulse rate substantially matches a resonant frequency of the cantilever so as to maintain optimal detection of IR absorption over a wide range of sample materials and set-up conditions. To achieve this, the inventors have developed several techniques to rapidly determine the contact and/or free resonances of a cantilever interacting with a sample surface.

One approach is to periodically sweep the modulation frequency of the IR source to find the maximum probe response. This technique works well on strong absorption peaks, but it may not work in regions of the sample or regions of a spectrum with weak absorption. In the case of a weak absorption it may be difficult to achieve enough signal-to-noise ratio to accurately optimize the IR source modulation frequency. Another approach is to include a mechanical or other actuator to excite the probe and then periodically sweep the frequency of the actuator to determine the peak response of the probe. Mechanical actuators, however, can excite a host of parasitic resonances which may not correspond to the resonance of the cantilever. Other common techniques include using a phase locked loop to constantly adjust the frequency of modulation to maintain a specific phase relation between the modulation and the response. This approach can work well for maintaining a cantilever in oscillation by an actuator, but this approach can fail if used to modulate an IR radiation source. The reason is if a region of the sample or a region of a spectrum has minimal absorption, there may not be sufficient signal strength for the PLL to operate.

To overcome these limitations, we have developed a technique that rapidly determines the true resonant frequency of the cantilever probe, free of parasitic resonances, and independent of the IR absorption of the sample. The technique involves performing a rapid thermal tune to determine the cantilever resonance. A thermal tune is a measurement of the cantilever noise spectrum excited by the thermal energy of the cantilever. Thermal tunes are commonly used in atomic force microscopy to estimate the cantilever spring constant for calibration of measured forces. A signal indicative of a deflection of the cantilever is sampled for a period of time. Then a fast Fourier transform (FFT) is performed on the deflection data to determine the cantilever response as a function of frequency. Due however to the small amplitude of cantilever motion, it has been necessary to average a large number of FFT amplitude response curves to obtain sufficient sensitivity to determine the cantilever resonance frequency and spring constant. Because of the large number of averages required, it has not been practical to measure thermal tunes at rapid rates. The inventors have developed techniques that allow rapid measurement of thermal tunes with sufficient frequency resolution to accurately tune the modulation rate of the IR source. These thermal tunes can be used by themselves or in combination with any of the other techniques described above.

Figure 1:
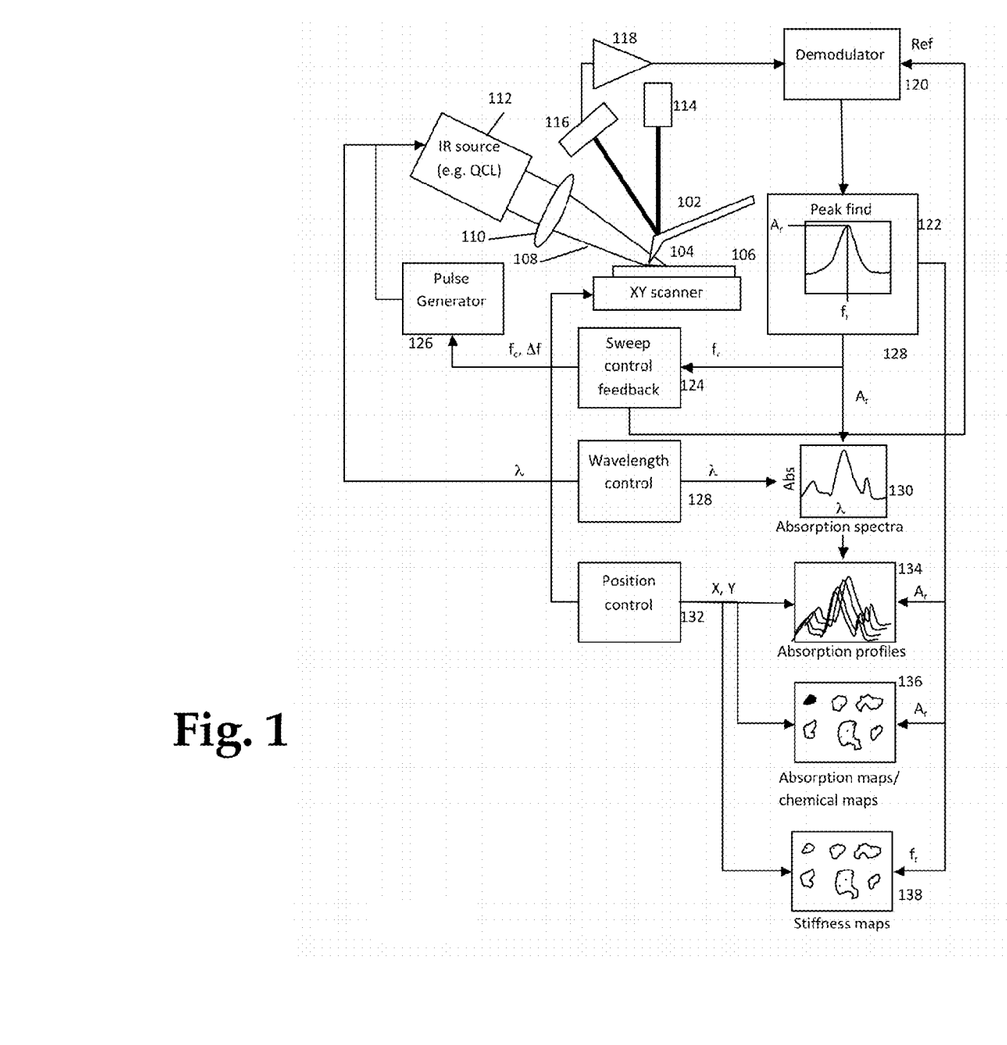
FIG. 1 is a simplified schematic diagram of an apparatus according to the current invention.

FIG. 1 shows an embodiment of the current invention. The invention will first be described in general terms, and then each component will be discussed in more detail below. AFM cantilever 102 with tip 104 is interacted with a surface of a sample 106. An IR light source 112 emits a beam 108 that is focused by one or more optical elements 110 to form a focus spot in the vicinity of the tip 104. A deflection detection system measures the probe response to light 108 incident on the sample. The deflection detection system may comprise an optical lever system, for example comprising a laser 114 and a photodetector 116, or one of the alternatives discussed below. Optionally the signal may be amplified, filtered or otherwise conditioned by amplifying electronics 118. The deflection detection system measures the probe response and creates a signal indicative of the cantilever motion. This signal is then sent to a demoduluator that creates at least one signal that is indicative of a characteristic of the oscillation of the cantilever.

A sweep controller 124 or pulse generator 126 may optionally send one or more reference signals to the demodulator to assist in determining the amplitude of the cantilever motion at a given frequency or range of frequencies. Next a peak find algorithm 122 may be used to determine one or more frequencies $f_r$ corresponding to peaks in the amplitude response of the cantilever. The peak frequency can be used for two different purposes. First, it can be sent to sweep controller 124 that may adjust the frequency range swept by the pulse generator 126. It may also be used to determine mechanical properties of the sample as discussed later in this specification. The function of the sweep controller 124 is to determine an optimal set of frequencies to be swept by the pulse generator. The strongest response of the cantilever will generally occur when the pulse repetition rate of the IR light source corresponds to a resonance of the cantilever. As mentioned previously, this frequency may not be constant in time or over the surface of the sample. Thus the pulse generator creates a series of trigger pulses to generate light pulses from IR light source 112 over a range of pulse repetition rates. The IR light source 112 may include a quantum cascade laser, but may also comprise any other source that can be pulsed or modulated at frequencies corresponding to cantilever resonances. In practice, this means frequencies 10 kHz or higher, and preferably 50 kHz or higher. It can be desirable in some cases to use even higher frequencies, for example in excess of 1 MHz. Such high frequencies can be used to excite resonance of stiffer cantilevers and/or excite higher modes of softer cantilevers. Stiffer cantilevers can in some cases be preferable as they can support both contact mode and non-contact/intermittent contact modes.

The pulse repetition rate of the light source 112, if tuned to a resonance peak of the cantilever, is generally not maintained at a fixed rate. The reason is that the resonance frequencies of the cantilever can change significantly over time and/or in its interaction with the sample surface. In the case of contact resonances, the peak frequencies can change by many kHz or tens of kHz or more due to changes in tip-sample force, temperature, electrostatic forces, tip-sample contact area, sample elastic modulus, sample damping, lateral forces and other factors. However even not in contact with the surface, the resonant frequency may shift due to thermal, viscous, electrostatic and other influences. To account for this, the current invention can dynamically sweep over a range of pulse repetition rates to find the rate that most efficiently excites a resonant response of the cantilever at a particular location on the sample and/or set-up conditions. That said, it is generally not desirable to spend a significant amount of time pulsing the IR light source off the resonant peak as this results in reduced signal-to-noise in the detection of IR absorption by the sample. The sweep controller 128 can dynamically adjust the center frequency $f_c$ and sweep width $\Delta f$ based on the variation in the peak frequency $f_r$ observed in the sample. For samples that are reasonably heterogeneous and with stable imaging conditions, the sweep width $\Delta f$ may be maintained very small, for example a few hundred Hz or even less. This is why the previously disclosed techniques can work without resonant frequency adjustment. In the case of a more heterogeneous sample, a sample with substantial topographic variations, or variable set-up conditions, the sweep width $\Delta f$ may be enlarged to ensure the sweep includes the peak frequency. These adjustments in center frequency and sweep width can be performed rapidly and repeatedly and preferably occur automatically without user intervention.

One challenge of the current invention is the possible absence of any detectable absorptions at any pulse frequency. The reason is that the IR absorption of a sample as a function of wavelength and absorption generally only occurs at wavelengths whose oscillation frequency corresponds to a molecular resonance. When there is a strong resonance, it can be easy to find the resonance peak frequency $f_r$ and maximum absorption $A_r$. But if there is weak or no absorption, it may be difficult to determine if the IR source is being pulsed at an optimal frequency. For this reason the current invention includes techniques for adaptively adjusting the center frequency and sweep width of the IR source modulation to adjust to different cantilever resonant conditions.

Figure 2:
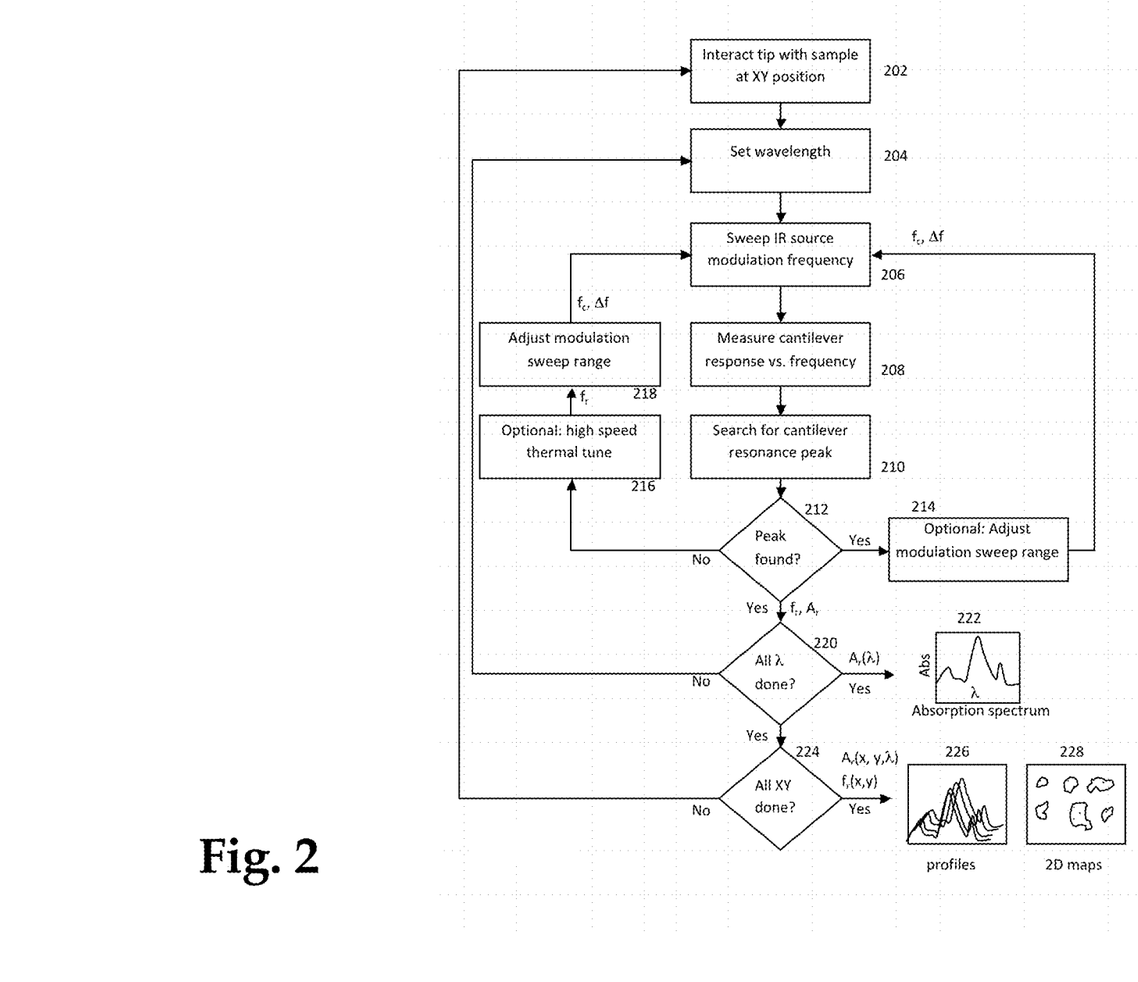
FIG. 2 is a simplified flow chart of a process under the current invention for measuring IR absorption of a region of a sample using a modulated IR source.

FIG. 2 shows a simplified flow chart of an embodiment of the current invention. The process starts (step 202) by interacting the AFM tip with a sample surface at a selected XY position. The IR light source is set to a desired wavelength (step 204) and directed at the region of the sample near the AFM tip. The IR light source is then pulsed or modulated over a plurality of frequencies, comprising a center frequency $f_c$ and a sweep width $\Delta f$. The cantilever motion is measured as a function of frequency (step 208), and a maximum response is searched for (step 210). Next we reach a decision point (212). In the case that a peak is found, the algorithm can output one or more peak frequencies $f_r$ and amplitudes $A_r$ that can be used to calculate spectra and absorption maps. Optionally, the system can attempt to refine the measurement and/or the subsequent measurement by adjusting the sweep range center frequency $f_c$ and a sweep width $\Delta f$ (step 214). The details of one embodiment of this adjustment are described in FIG. 3. If, on the other hand, an absorption peak is not found ("No" terminal on decision block 212), the system can dynamically search for the resonance peak. There are two main causes of no peak being detected. In one case, the cantilever resonance frequency may have shifted outside the current modulation sweep range. In this case, the sweep width $\Delta f$ can be increased and/or the modulation center frequency $f_c$ can be adjusted to find the peak (step 218). In another case, there may be insufficient absorption by the sample at the selected wavelength to create a detectable cantilever response. As a check for this case, the system controller can optionally perform a high speed thermal tune. This is a technique, described below, that detects cantilever vibration resulting from thermal energy from the ambient environment. This motion occurs at all frequencies, but is accentuated near cantilever resonances. The inventors have developed a technique for very high speed measurements of cantilever resonant frequency using a thermal method. Using this technique a cantilever resonance can be detected with a sensitivity of <200 Hz within 100 msec. As such this measurement can be used to rapidly recenter the IR source modulation frequency, even in the absence of IR absorption. The normalized value of $A_r$ along with resonance frequency $f_r$ may be accumulated at a plurality of wavelengths λ (step 220) and/or XY positions (step 224) until all desired points are measured. Note that it can be useful to perform measurements at a single wavelength, a single XY location or any combination of multiple wavelengths and positions.

Once the system has determined one or more peak resonance frequencies and amplitudes $f_r$ and $A_r$, an optional normalization step may be performed (not shown). This normalization step can scale the measured resonance amplitude $A_r$ by the modulation frequency sweep width used to find the resonance peak. This ensures that the amplitude scales are the same for different wavelengths and/or XY sample positions where a narrower or wider modulation sweep may have been performed. At this point several useful outputs can be created including absorption spectra (222), absorption profiles (226), and 2D maps (228) of IR absorption, chemical composition, contact resonance frequency, damping, stiffness and other properties.

Figure 3:
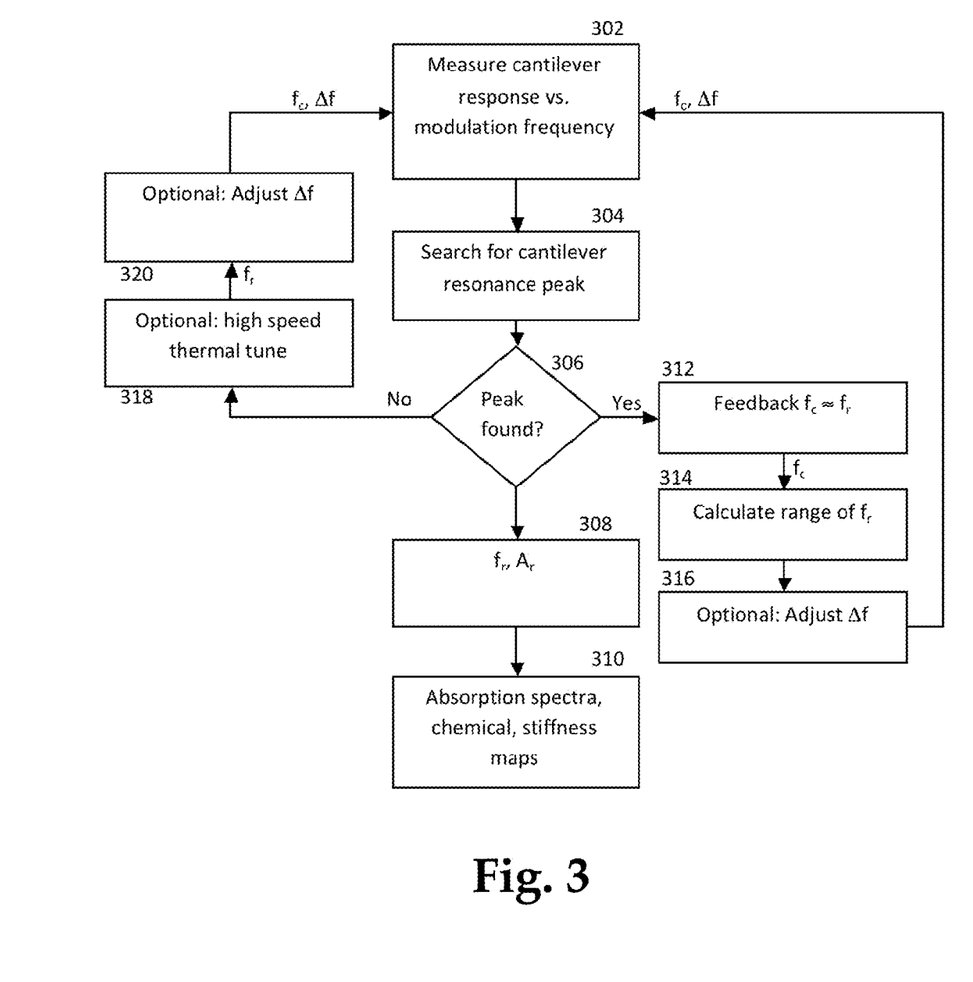
FIG. 3 is a simplified flow diagram for a process of selecting the modulation center frequency and sweep range under the current invention.

FIG. 3 shows some additional details of an embodiment to optimally choose the modulation frequency sweep. The motivation for this portion of the invention is to spend the minimal amount of time modulating the IR light source at frequencies that don't correspond to a region where there is resonant enhancement from the cantilever oscillation. In other words, we wish to maximize the fraction of time spent oscillating on the cantilever resonance. To achieve this the cantilever response to IR radiation is measured as a function of modulation frequency (302). Next the system searches for a resonance peak using one or more methods described above or in the alternate embodiments section below. If a peak is found, a decision point 306 can call a feedback loop 312 to attempt to adjust the center frequency $f_c$ of the modulation frequency sweep to roughly center the resonance frequency $f_r$. The feedback loop may be as simple as directly setting $f_c = f_r$, or it may employ a feedback loop like a PID loop or more complex feedback algorithms that can make an adjustment to $f_c$ using both the instantaneous $f_r$ and a set of previous $f_r$ measurements. Simple integral feedback can work well as it smoothes out noise in the measured resonant frequencies $f_r$ but will attempt to drive over time to a negligible error. Note in this case of employing a feedback loop the process variable can be the $f_r$-$f_c$, the difference between the detected resonance frequency $f_r$ and the center frequency of the modulation sweep, $f_c$. The setpoint for this process variable is generally around zero, such that $f_c \approx f_r$. Then the output of the feedback loop is the center frequency for the next modulation frequency sweep.

A feature of the current invention is that the modulation frequency sweep can adapt in real-time to the conditions it encounters (step 316). For example the system can accumulate and analyze the range of resonant frequencies detected (or equivalently center frequencies output). If the range of the measured resonant frequencies or center frequencies used is small compared to the sweep width ($\Delta f$), the sweep width can be dynamically reduced. This allows more time to be spent where the IR source is productively exciting the cantilever resonance. If there is a large spread in the resonance frequencies or center frequencies, the system can dynamically expand the frequency sweep width $\Delta f$ to ensure the resonance peak is found. It is also possible to perform a multiple stage sweep, for example a coarse sweep to roughly find the peak location and then a fine sweep to find the peak resonance with high accuracy and maximal time spent near the resonance. In addition, in heterogeneous samples there may be a small number of center frequencies which differ significantly. In this case, the frequency sweep width could be kept small but cover ranges about each of these center frequencies.

As mentioned previously, under some conditions the IR illumination may not generate a cantilever response sufficiently large to detect. In this case the system may either perform a thermal tune (318) and/or broaden the modulation sweep width (320). As before, once the peaks are found with sufficient fidelity, the cantilever amplitudes and resonant frequencies can be analyzed as a function of wavelength, position to generate absorption spectra, spatially resolved spectral profiles, and/or maps of absorption, composition, contact resonant frequency, and/of stiffness or related measurements.

Rapid Thermal Tunes

Figure 4:
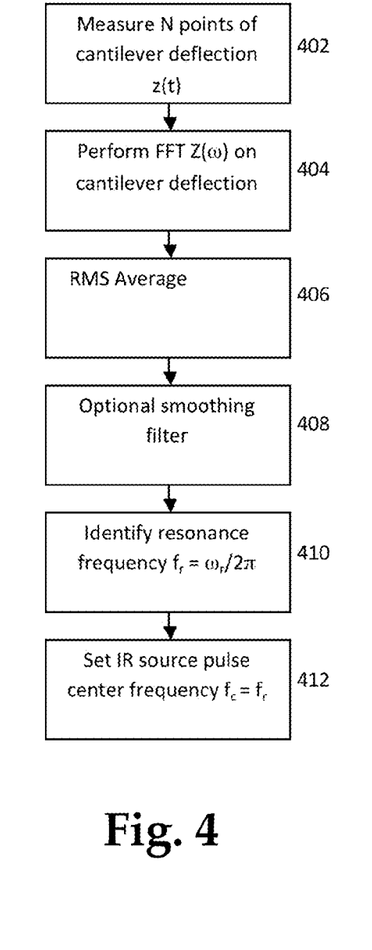
FIG. 4 is a simplified flow diagram of a method for a high speed thermal tune to determine a resonant frequency of a cantilever

We have implemented a technique to rapidly measure thermal tunes with sufficient accuracy to maintain desired synchronization of the IR source modulation with the cantilever resonance. This technique can also be used to measure local stiffness of the sample via contact resonant frequency measurements, without external actuation of the cantilever. In one embodiment, the thermal tune technique works in the following way as outlined in FIG. 4. A signal indicative of a deflection of the cantilever z(t) is sampled for a short period of time (step 402). For example in one embodiment we have sampled 100,000 data points at 10 MHz sample rate, e.g. a burst of 0.01 seconds. Next an FFT is performed (step 404) on the deflection data to convert z(t) into $Z(\omega)$. With 100,000 points, at 10 MHz, a frequency resolution of 100 Hz is achieved. Next we perform root mean square (RMS) averaging on a series of FFTs (step 406) The RMS average averages the quantity $<Z^*Z>$, where Z is the FFT $Z(\omega)$ of the cantilever deflection signal. The RMS average does not strictly improve the signal to noise ratio (peak amplitude to baseline average), but it does dramatically suppress the fluctuations as a function of frequency, thus allowing more robust identification of the peak resonance frequencies. Other signal averaging schemes can also be employed, for example direct averaging of the FFT amplitude spectra. A smoothing filter, for example a Savitzky-Golay filter can optionally be employed (step 408) to further smooth the data before localization of the of the peak frequency. Many other smoothing filters could also be used. Next a peak resonance frequency $f_r$ is identified using any of the techniques described elsewhere (step 410). Finally, the center frequency $f_c$ of the IR source modulation can be set to the cantilever resonance frequency $f_r$ (step 412). It should be noted that this technique works equally well for both cases where the cantilever is in contact with the surface or not in constant contact with the surface.

Figure 5:
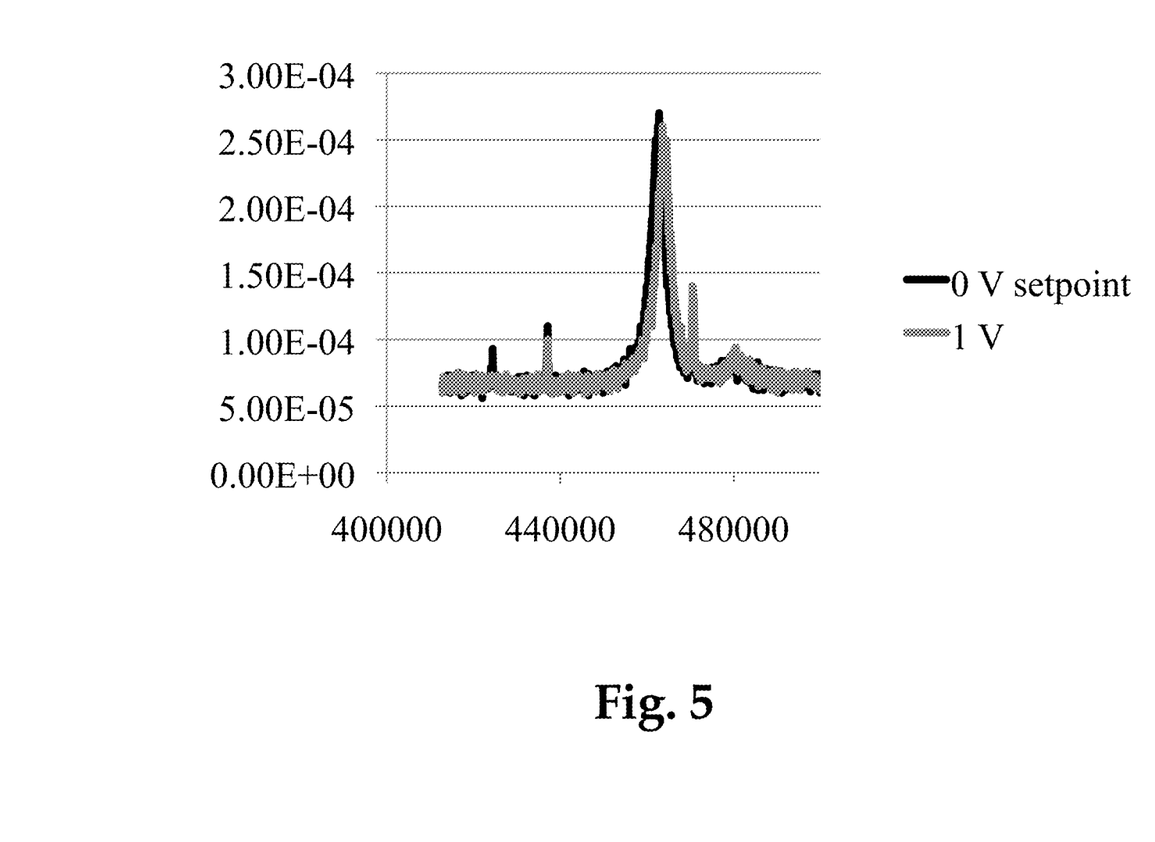
FIG. 5 is an example of a high speed thermal tune of a cantilever

Two example thermal tunes are shown in FIG. 5. These were acquired with 10 RMS averages, and a total measurement time of around 0.1 sec. The two thermal tunes were taken at different setpoint forces—the shift due to a difference in contact areas is easily detected.

Figure 6:
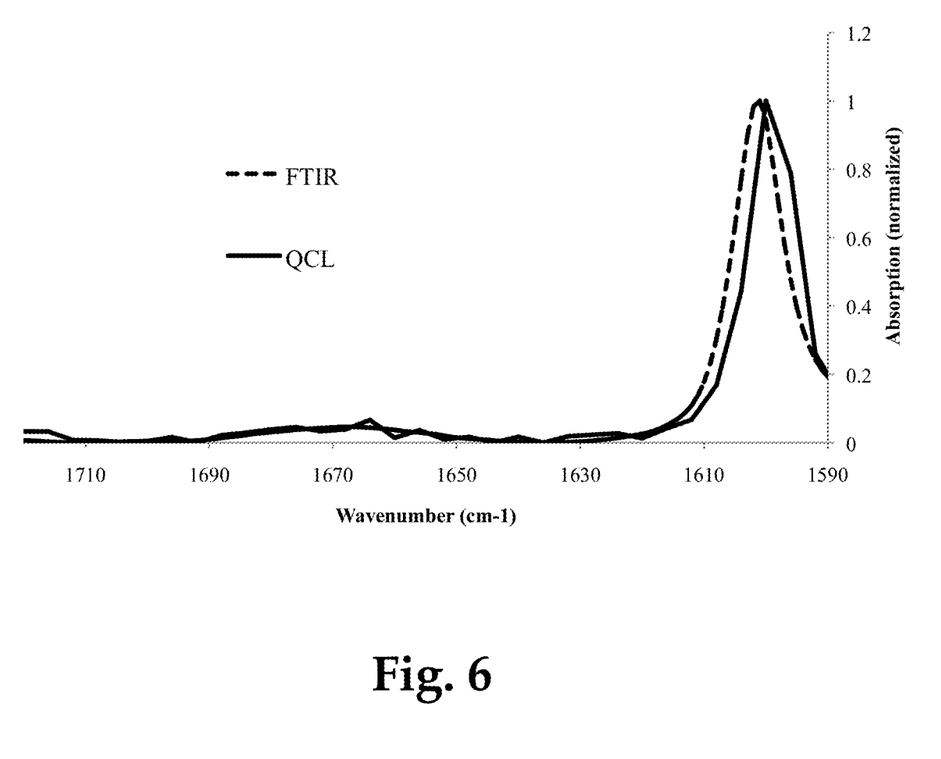
FIG. 6 is an example of an absorption spectrum obtained with the current invention.

FIG. 6 shows an IR absorption spectrum obtained under the current invention. This figure shows an IR absorption spectrum obtained on a sample of polystyrene. A contact mode cantilever, model SICON from Applied Nanostructures was used. This cantilever has a nominal spring constant of 0.2 N/m and a free resonance around 12 kHz. Measurements were performed at the first contact resonance that was around 40 kHz and are labeled "QCL." The measurement shows good agreement to conventional IR spectroscopy (labeled "FTIR").

Figure 7:
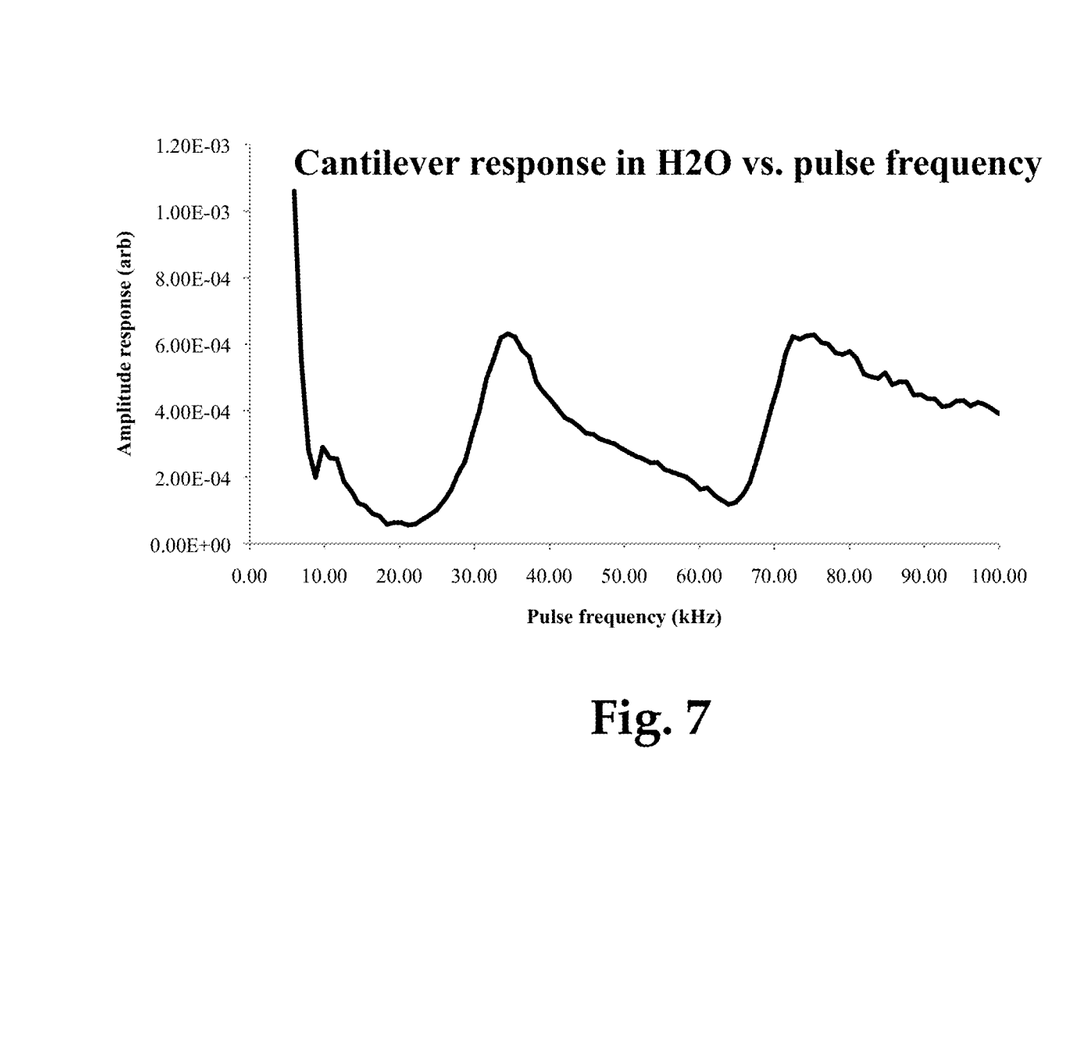
FIG. 7 is an example of an absorption map obtained with the current invention.
Figure 8:
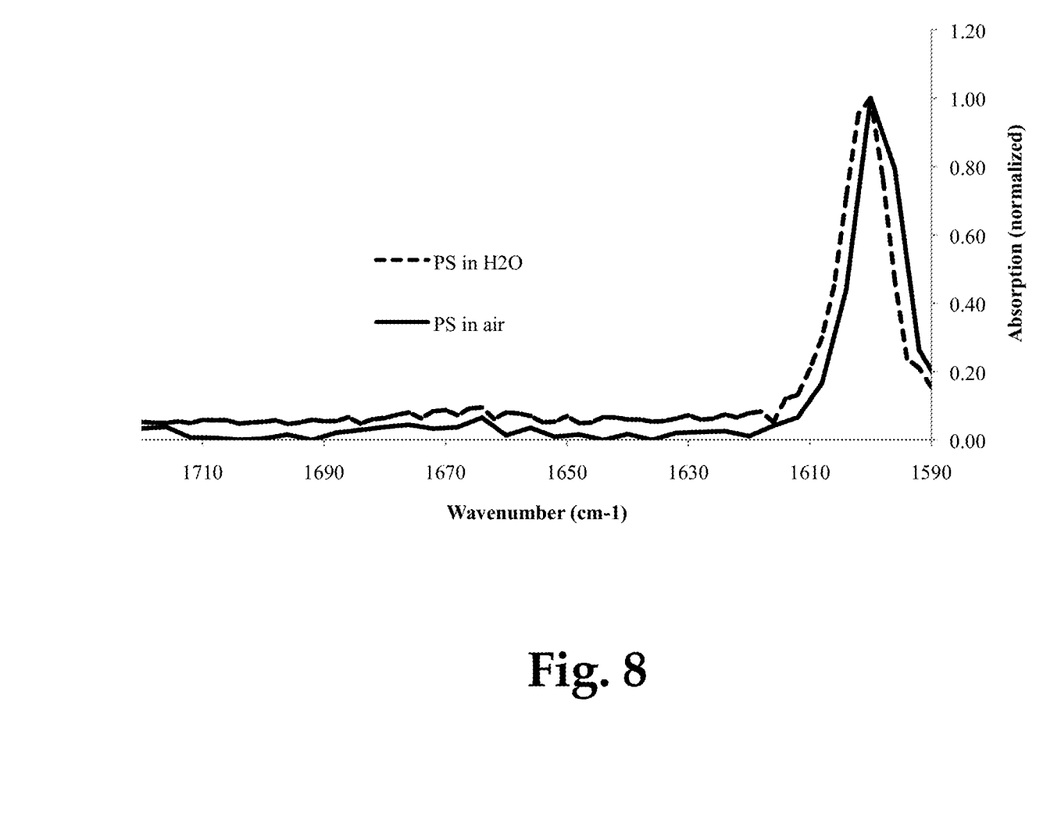
FIG. 8 is an example of a contact resonance/stiffness map obtained with the current invention.

We have also performed measurements with cantilevers and samples immersed in liquid under the current invention. In conventional AFM-IR, this type of measurement is difficult in part due to the large hydrodynamic damping of the liquid that heavily damps transient resonance response used in the prior art. Under the current invention, the IR source is pulsed in synch with the cantilever resonance, allowing generation of continuous oscillation that can overcome the damping. FIG. 7 shows an example measurement of cantilever response on a sample of polystyrene with the sample and cantilever immersed in water. FIG. 8 shows a comparison of absorption spectra obtained under the current invention with the sample in water (dashed line) and in air (solid line).

Figure 9:
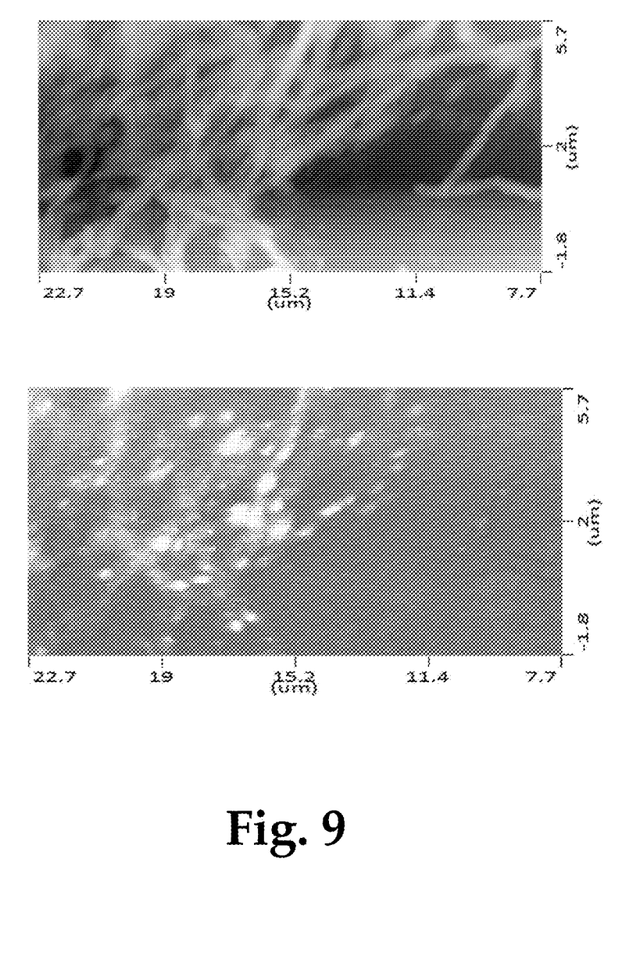

We have also used the current invention to perform spatially resolved maps of chemical species on a biological sample. This can be a significant challenge because the contact resonance frequency dramatically shifts on such samples due to variations in elasticity and tip-sample contact area. FIG. 9 shows an AFM topography image (top) and an IR absorption (bottom) on streptomyces bacteria. The measurements were made by rapidly sweeping the pulse repetition rate of a QCL to determine a frequency of optimal cantilever response. The frequency was continuously adjusted and the peak amplitude response was recorded at each XY pixel. For this sample the contact resonance varied from roughly 35 to 45 kHz over the sample.

Alternate Embodiments

This section outlines various alternative embodiments for components of the current invention. First, when the AFM tip is interacted with the sample, the tip-sample interaction can be attractive, repulsive, or a combination of both. The AFM may operate in contact, non-contact, intermittent contact, tapping, pulsed-force mode and/or other modes of AFM operation, all of which may experience drift in probe resonant frequency over time. Thus it is important to note that the need for, and the operation of, the invention apply for other than just contact resonance scenarios.

IR light from the IR light source is used to illuminate a region of the sample. In between the source and the sample there may be a large variety of optical elements to shape the beam, adjust its angle, polarization, wavelength range, etc. There may also be elements like optical fibers to direct the beam from a remote location. There may also be additional elements in the beam path, especially close to the sample, to locally enhance the strength of the fields generated by the incident radiation. The focusing optical elements 110 may comprise one or more lenses and/or mirrors or diffractive optics that can focus IR radiation. The deflection detection system may comprise an optical lever system, for example comprising a laser 114 and a photodetector 116. The deflection detection system can also comprise many other AFM deflection measuring schemes including for example other optical, interferometric, Doppler vibrometry, capacitive, inductive, piezoresistive, piezoelectric, and thermal detection techniques. One or more of these techniques is used to create a signal indicative of the cantilever motion. This signal may be related to the position, deflection, bend angle, velocity, oscillation amplitude or other properties of the cantilever motion. The demodulator 120 creates a signal may be indicative of the amplitude, phase, in-phase component (X), quadrature component (Y), or similar measurements of the cantilever's AC motion. The demodulator may comprise an RMS-to-DC converter, a lock-in amplifier, and/or a Fast Fourier Transform or other demodulation means that extract oscillation amplitudes at one or more frequencies. The demodulator may be implemented in analog electronics, digital electronics, and/or implemented in software. In the case of a software implementation, the demodulator may be programmed on an embedded controller, a digital signal processor, a field programmable gate array, other programmable logic devices, and/or a personal computer. The demodulator may also have its functions distributed across multiple hardware and software platforms.

In one embodiment a resonant peak frequency $f_r$ can be identified by analyzing an amplitude versus frequency curve. A peak frequency $f_r$ can be found by determining a maximum amplitude response in an range of frequencies, or by fitting a model through a portion of the amplitude versus frequency curve. For example, one can fit a Lorentzian function, a Gaussian function or any peak shaped functions. With high signal to noise, small numbers of data points can be used for peak fitting. For example very efficient algorithms can be used to detect peak frequencies with resolution below the FFT bin size using a Gaussian or parabolic peak fit through the three highest points. These techniques have the advantage of being computationally very efficient with no requirement for iterative curve fitting. Another method of determining the contact resonance frequency with high noise rejection is to employ a peak centroid measurement. In one implementation one can determine a centroid frequency where the integral from a start frequency to the centroid frequency has half the area of the integral from a start frequency to an end frequency. This technique can provide useful measurements of the contact resonance frequency and its trends with temperature even when the individual frequency response measurements may be too noisy to determine a contact resonance frequency from the maximum cantilever response amplitude. The peak frequency $f_r$ can also be determined selecting a frequency with a desired phase (e.g. when the phase crosses 90°).

In one embodiment the IR source is pulsed with short pulse durations, from 1 nsec to 100 nsec. But it is also possible to use longer pulses and or continuous wave IR sources that are modulated sinusoidally instead of pulsed. In this case the techniques described above for sweeping the pulse repetition rate can be applied to sweeping the sinusoidal modulation frequency. In this specification and associated claims, the term "modulation" is intended to cover repetitive pulsed operation and/or sinusoidal modulation and/or other arbitrary generation of IR light whose intensity is periodically altered. "Modulation frequency" thus refers to at least one Fourier frequency component of the modulation. In this case of a sinusoidal modulation, the modulation frequency would be the frequency of the sine wave. In the case of a repetitive string of pulses, the frequency would correspond to at least one Fourier component of the pulse train. In the simplest case, the modulation frequency would be the pulse repetition rate, or the reciprocal of the pulse repetition period. But it is also possible to operate such that a higher harmonic of the pulse repetition rate is used to excite a cantilever resonance. For example, a short pulse at 10 kHz will have harmonic components at 20, 30, 40 kHz, etc. Any of these higher harmonics can also be selected to excite resonant oscillation of a cantilever.

The determination of a cantilever resonant frequency by any of the techniques described above can also be used to measure and map viscoelastic properties of the sample surface. Cantilever resonant frequency peak positions and peak shapes can sensitively depend on sample elastic modulus, friction, adhesion, dissipation, and other properties. By measuring the resonance frequency as a function of position, it is possible to make a map of the variations in elastic properties of a sample. With additional information from the peak width and/or quality factor, it is possible to extract viscoelastic and/or damping information including storage and loss modulus, tan(delta), and other properties.

In one embodiment the vertical contact resonant frequency can be determined by monitoring the lateral contact resonant frequency. Certain effects (changes in sample elasticity, changes in normal force, etc.) should cause shifts in the lateral contact resonant frequency that are related to the shift in the vertical resonant frequency. The lateral resonant frequency can be determined by performing the above described thermal tune function on the lateral signal from the deflection detection system. Alternatively the lateral resonant frequency could be excited by a modulation or impulse to generate larger amplitudes and therefore faster or more accurate determinations of the lateral resonant frequency. Once the lateral resonant frequency is determined the correct modulation frequency can be determined based on characterization of the correlation factors between the two values and then this frequency used to modulate the IR source.

In one embodiment the contact resonant frequency can be tracked using the relationship between the normal force and the contact resonant frequency. As shown in FIG. 5, the contact resonant frequency will shift higher with increased force. By modulating or stepping the normal force applied to the cantilever the amplitude at a fixed frequency will change. This can be accomplished by shifting the relative positions of the sample and the probe support such that the normal force applied by the probe tip changes or alternatively by the application of an external force on the probe such as an electrostatic force. By measuring the amplitude and phase of the change in oscillation amplitude of the probe relative to the change in force it can be determined whether the modulation frequency is centered on the contact resonant frequency or on the low or high side. Then the modulation frequency can be adjusted to center it on the contact resonant frequency or alternatively maintain some fixed position in terms of the amplitude and phase relationship.

We claim:

1. A method of obtaining measurements of infrared absorption of sub-micron regions of a sample with a probe microscope employing a cantilever probe with a tip, the method comprising:
   a) illuminating a region of a sample with a tunable source of infrared radiation;
   b) interacting the probe tip with a surface of the sample;
   c) adjusting repeatedly a modulation frequency of the source of infrared radiation such that the modulation frequency substantially overlaps a resonant frequency of the cantilever probe and remains substantially overlapped as the cantilever resonant frequency shifts;
   d) measuring a probe response resulting from absorption of infrared radiation by the sample.

2. The method of claim 1 wherein the resonant frequency corresponds to a contact resonance of the cantilever probe in contact with the sample surface.

3. The method of claim 2 wherein the contact resonant frequency of the cantilever probe is selected by performing a thermal tune of the cantilever probe.

4. The method of claim 3 wherein the thermal tune is performed in less than 1 second.

5. The method of claim 3 wherein the thermal tune is performed in less than 0.1 seconds.

6. The method of claim 3 wherein the thermal tune is performed by:

a. recording data indicative of a deflection of the cantilever over a period of time;
   b. performing a fast Fourier transform on the data;
   c. repeating steps a) and b);
   d. averaging the fast Fourier transforms using root mean square averaging;
   e. identifying a resonant frequency of the cantilever probe from a peak in the averaged fast Fourier transform.

7. The method of claim 1 wherein the tunable source of infrared radiation is at least one of a quantum cascade laser and an optical parametric oscillator.

8. The method of claim 1 wherein step d) is repeated at a plurality of wavelengths of the tunable source of infrared radiation to create an absorption spectrum of the submicron region of the sample.

9. The method of claim 1 wherein step d) is repeated at a plurality of positions on the sample surface to create an absorption map of the sample surface.

10. The method of claim 1 comprising covering the surface of the sample in fluid so that the tip-sample interaction is within fluid.

11. A method of obtaining measurements of infrared absorption of sub-micron regions of a sample with a probe microscope employing a cantilever probe with a tip, the method comprising:
    a. illuminating a region of a sample with a quantum cascade laser;
    b. interacting the probe tip with a surface of the sample;
    c. measuring a thermal tune of the cantilever probe to determine a contact resonant frequency of the cantilever probe;
    d. adjusting a pulse frequency of the quantum cascade laser such that the pulse frequency substantially overlaps a resonant frequency of the cantilever probe;
    e. measuring a probe response resulting from absorption of infrared radiation by the sample.

12. The method of claim 11 further comprising the step of repeating steps a-e so as to account for contact resonant frequency shifts of the cantilever probe.

13. The method of claim 12 wherein the contact frequency shifts are due to variations in at least one of: sample elastic modulus, tip-sample contact area, normal tip-sample force, or lateral tip-sample force.

14. The method of claim 11 comprising covering the surface of the sample in fluid so that the tip-sample interaction is within fluid.

* * * * *